US011052027B2

(12) United States Patent
Erkens et al.

(10) Patent No.: US 11,052,027 B2
(45) Date of Patent: Jul. 6, 2021

(54) USE OF SODIUM CHLORIDE IN BLEACHING AGENTS BASED ON PERCARBONATE FOR HUMAN HAIR APPLICATION

(71) Applicant: Henkel AG & Co. KGaA, Duesseldorf (DE)

(72) Inventors: Udo Erkens, Willich (DE); Phillip Jaiser, Langenfeld (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/721,711

(22) Filed: Dec. 19, 2019

(65) Prior Publication Data
US 2020/0206104 A1   Jul. 2, 2020

(30) Foreign Application Priority Data

Dec. 28, 2018  (DE) ..................... 10 2018 133 661.6
Dec. 28, 2018  (DE) ..................... 10 2018 133 668.3
Dec. 28, 2018  (DE) ..................... 10 2018 133 685.3
Dec. 28, 2018  (DE) ..................... 10 2018 133 688.8
Feb. 28, 2019  (DE) ..................... 10 2019 105 149.5
Sep. 24, 2019  (DE) ..................... 10 2019 214 516.7

(51) Int. Cl.
*A61Q 5/00* (2006.01)
*A61K 8/22* (2006.01)
*A61Q 5/08* (2006.01)
*A61K 8/19* (2006.01)
*A61K 8/20* (2006.01)

(52) U.S. Cl.
CPC .................. *A61K 8/22* (2013.01); *A61K 8/19* (2013.01); *A61K 8/20* (2013.01); *A61Q 5/08* (2013.01)

(58) Field of Classification Search
CPC ... A61Q 5/08; A61K 8/22; A61K 8/19; A61K 2800/31; A61K 8/022; A61K 8/20; A61K 31/327
USPC .......................................................... 424/62
See application file for complete search history.

(56) References Cited

U.S. PATENT DOCUMENTS

| 4,326,976 A | * | 4/1982 | Logan | ................. | C11D 3/3937 510/375 |
| 2007/0037729 A1 | * | 2/2007 | Mathur | ..................... | C11D 3/10 510/507 |
| 2011/0232669 A1 | * | 9/2011 | Suenger | .................... | A61K 8/44 132/208 |
| 2012/0207689 A1 | * | 8/2012 | Konno | ..................... | A61K 8/22 424/62 |

FOREIGN PATENT DOCUMENTS

| DE | 19756454 C1 | 6/1999 |
| GB | 2570782 A | 8/2019 |
| JP | H09143051 A | 6/1997 |
| RU | 2180222 C2 | 3/2002 |
| WO | 2011150138 A1 | 12/2011 |

OTHER PUBLICATIONS

CN 1059229 C (Abstract) dated Dec. 2000.*
JP 201803925 (Abstract) dated Mar. 2018.*
Mintel GNPD: "Permanent Hair Color Powder", Record ID 6980173, Published Oct. 2019, www.mintel.com.

* cited by examiner

*Primary Examiner* — Eisa B Elhilo
(74) *Attorney, Agent, or Firm* — Lorenz & Kopf, LLP

(57) ABSTRACT

The subject of the present disclosure is a blonding agent for changing the natural color of keratinic fibers, in particular human hair, which contains a) sodium percarbonate, b) sodium chloride and further from 0 to about 8% by weight of water. Furthermore, the present disclosure relates to a method for blonding human hair.

16 Claims, No Drawings

USE OF SODIUM CHLORIDE IN BLEACHING AGENTS BASED ON PERCARBONATE FOR HUMAN HAIR APPLICATION

CROSS-REFERENCE TO RELATED APPLICATION

This application claims priority to German Patent Application No. 10 2019 214 516.7, filed Sep. 24, 2019, German Patent Application No. 10 2019 105 149.5, filed Feb. 28, 2019, German Patent Application No. 10 2018 133 668.3, filed Dec. 28, 2018, German Patent Application No. 10 2018 133 685.3, filed Dec. 28, 2018, German Patent Application No. 10 2018 133 661.6, filed Dec. 28, 2018, and German Patent Application No. 10 2018 133 688.8, filed Dec. 28, 2018, in which all are incorporated herein by reference in their entirety.

TECHNICAL FIELD

The present disclosure relates to blonding agents which serve as a lightening agent for keratinic fibers, in particular human hair. Furthermore, a method for the oxidative lightening of keratinic fibers using the blonding agent.

BACKGROUND

The lightening of one's own hair has always been the desire of many consumers, since a blond hair color is considered attractive and fashionable in terms of desirability. Various blonding agents having different blonding performance are available in the market for this purpose. The oxidizing agents contained in these products are able to lighten the hair fiber by the oxidative destruction of the hair's own melanin. For a moderate blonding effect, the use of hydrogen peroxide, optionally with the use of ammonia or other alkalizing agents, is sufficient as the oxidizing agent alone. To achieve a stronger blonding effect, a mixture of hydrogen peroxide and at least one compound selected from percarbonates and persalts, in particular peroxodisulfate salts and/or peroxomonosulfate salts, is usually used. To enhance the blonding effect, the agents contain higher use concentrations of hydrogen peroxide and percarbonates or persalts, in particular persulfates. Dark, dark brown or black hair can be lightened in one step by from about 4 to about 6 shades. The hydrogen peroxide and the percarbonates or persalts are kept separate from each other until use so as not to prematurely deactivate the percarbonates or persalts. The hydrogen peroxide component, which comprises an aqueous solution of hydrogen peroxide, has an acidic pH value, in particular a pH value of from about 2.5 to about 5.5, in particular from about 3 to about 5, for the stabilization of the hydrogen peroxide, in each case measured at 20° C.

For the melanin degrading effect of the hydrogen peroxide and the blonding action on the keratinic fiber, however, it is advantageous when the application mixture of hydrogen peroxide solution and persalt has an alkaline pH value, preferably lying in the range of from about 8 to about 12, particularly preferably in the range of from about 8.5 to about 11.5, most preferably in the range of from about 9 to about 10.5, each measured at 20° C.

There are several possibilities for setting an alkaline pH value of the lightening application mixture: The blonding powder contains, in addition to the at least one persalt or percarbonate, at least one powdered alkalizing agent in such a total amount that the application mixture has the desired alkaline pH value; or the hydrogen peroxide solution is combined not only with the blonding powder but additionally with an alkalizing agent formulation for the application mixture.

If the alkalizing agent preparation and/or the blonding powder are added to oxidation dye precursors and/or direct acting dyes, the hair can be dyed at the same time. Corresponding 3-component hair coloring agents are offered in particular for consumers with very dark melanin-rich hair.

However, the lightening is also accompanied by hair damage, since not only the dyes of the hair, but also the structural constituents of the hair, are oxidatively damaged. Depending on the severity of the degree of damage, this ranges from rough, brittle and difficult to comb hair to a reduced durability and tear resistance of the hair up to hair breakage. The greater the amount of hydrogen peroxide used and optionally the persalts or percarbonates, the greater the damage is therefore usually caused on the keratinic fibers.

In order to minimize the hair damage and to compensate for the damaging effect of the oxidizing agents, attempts have always been made to find formulations which ensure good blonding performance with little hair damage.

BRIEF SUMMARY

Blonding agents for changing the natural color of keratinic fibers and methods for lightening keratinic fibers are provided herein. In an embodiment, a blonding agent for changing the natural color of keratinic fibers includes:
  a) sodium percarbonate,
  b) sodium chloride and further
  c) from 0 to about 8% by weight of water based on the weight of the blonding agent.

In another embodiment, a method for lightening keratinic fibers is provided wherein a blonding agent (B) as described above is mixed with water, applied immediately afterwards to the keratin-containing fibers, left on the fibers for from about 5 to about 60 minutes and then the fibers are rinsed with water and optionally washed with a surfactant-containing detergent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was therefore the object of the present disclosure to provide agents for lightening or blonding keratinic fibers, in particular human hair, which damage the keratinic fibers as little as possible and which are easy to prepare and to handle. In particular, the present disclosure has for its object to keep the concentration of active ingredients for blonding, that is, the concentration of organic or inorganic peroxides and/or percarbonates, at a level used in commercial products, wherein the blonding effect is improved.

Surprisingly, the objects underlying the present disclosure were achieved by the subject matter of claim 1. A first subject of the present disclosure is therefore a blonding agent for changing the natural color of keratinic fibers, in particular human hair, that contains sodium percarbonate, sodium chloride and further from 0 to about 8% by weight, preferably from about 0.1 to about 5% by weight, particularly preferably from about 0.5 to about 3% by weight of water, in each case based on the weight of the blonding agent.

As contemplated herein, keratinic fibers are understood to mean furs, wool, feathers and in particular human hair. Although the agents as contemplated herein are primarily suitable for blonding and lightening keratinic fibers, in principle, there is nothing to prevent their use in other fields as well.

The blonding agent as contemplated herein contains, as a first essential constituent, at least one oxidizing agent which comprises sodium percarbonates. Sodium percarbonates are understood to mean sodium carbonate-hydrogen peroxide complexes. Commercially available sodium percarbonate has the average composition $2Na_2CO_3 \cdot 3H_2O_2$. Sodium percarbonate is present as a white, water-soluble powder which readily decomposes into sodium carbonate and bleaching and oxidizing "active" oxygen.

According to a preferred embodiment of the present disclosure, sodium percarbonate is present in the blonding agent in an amount of from about 1-50% by weight, preferably from about 2-12% by weight, particularly preferably from about 4-10% by weight, most preferably from about 6-8% by weight, in each case based on the weight of the blonding agent.

The blonding agent as contemplated herein contains sodium chloride as a second essential constituent. It has surprisingly been found that a significant increase in the lightening performance can be achieved by the use of sodium chloride. The blonding performance is improved at the same concentration of inorganic and organic peroxides and percarbonates and the otherwise same blonding method when sodium chloride is present in the blonding agent. It can be presumed that the polarity of the liquid medium when mixing the ready-to-use mixture and lumping when mixing the mixture is prevented.

According to a preferred embodiment of the present disclosure, sodium chloride is present in an amount of from about 0.1-5% by weight, preferably from about 0.2-4% by weight, more preferably from about 0.3-3% by weight, even more preferably from about 0.4-1.5% by weight, most preferably from more than about 0.5 to less than about 0.7% by weight, in each case based on the weight of the blonding agent. Sodium chloride can be present in an amount of about 0.5% by weight or more than about 0.5% by weight to about 5% by weight in the blonding agent or sodium chloride can be present in an amount of more than about 0.5% by weight to about 5% by weight in the blonding agent.

The blonding agent is preferably a blonding powder which is an anhydrous, powdered oxidizing agent preparation containing at least one sodium percarbonate and sodium chloride. According to claim 1, the blonding agent contains from 0 to about 8% by weight, preferably from about 0.1 to about 5% by weight, particularly preferably from about 0.5 to about 3% by weight of water, in each case based on the weight of the blonding agent, so that, as contemplated herein, it can be referred to as "anhydrous". This specification refers to the content of free water. Not taken into account is the content of molecularly bound water or water of crystallization which individual powder constituents can have. The water content can be determined, for example, based on ISO 4317 (version 2011-12) by employing Karl Fischer titration.

As contemplated herein, the term "powder" or "powdered" is to be understood to mean a free-flowing dosage form of individual particles which is solid at 20° C. and 1013 mbar and in which the individual particles have particle sizes in the range from about 0.1 µm to a maximum of about 1.6 mm. The determination of the particle sizes can preferably be carried out by employing laser diffraction measurement in accordance with ISO 13320-1 (2009). Optionally, the particles can be adapted in their grain size by physical treatment, such as sieving, pressing, granulating or pelleting, or by the addition of certain excipients, to the requirements of the blonding powder, for example, to enable a better miscibility of the individual powder constituents or the miscibility of blonding powder with an aqueous solution.

Blonding agents preferred as contemplated herein have a bulk density in the range of from about 500 to about 1000 g/l (grams/liter), preferably from about 550 to about 900 g/l, particularly preferably from about 600 to about 820 g/l. The determination of the bulk density is preferably carried out according to EN ISO 60 (version 01/2000) or DIN ISO 697 (version 01/1984).

Unless otherwise indicated, state references refer to standard conditions, that is, to a temperature of 25° C. and a pressure of $10^5$ Pa.

According to a further preferred embodiment, the blonding agent contains, as a further constituent, at least one inorganic salt of a peroxosulfuric acid. Peroxosulfuric acids are understood to mean peroxodisulfuric acid and peroxomonosulfuric acid (Caro's acid).

Preferably, the at least one inorganic salt of a peroxosulfuric acid is selected from ammonium peroxodisulfate, alkali metal peroxodisulfates, ammonium peroxomonosulfate, alkali metal peroxomonosulfates, and alkali metal hydrogen peroxomonosulfates. Particularly preferred are ammonium peroxodisulfate, potassium peroxodisulfate, sodium peroxodisulfate and potassium hydrogen peroxomonosulfate. In particular, the at least one inorganic salt of a peroxosulfuric acid is selected from sodium peroxodisulfate, potassium peroxodisulfate, ammonium peroxodisulfate, sodium peroxomonosulfate, potassium peroxomonosulfate, ammonium peroxomonosulfate, and mixtures of these compounds.

Furthermore, It has proved to be particularly preferred in the work of the present disclosure when the blonding powder as contemplated herein contains at least two or three different peroxodisulfates. Preferred peroxodisulfate salts in this case are combinations of ammonium peroxodisulfate and potassium peroxodisulfate or sodium peroxodisulfate, in particular the combination of ammonium peroxodisulfate and potassium peroxodisulfate and sodium peroxodisulfate.

The total amount of inorganic salt of a peroxosulfuric acid is from about 1-80% by weight, preferably from about 10-70% by weight, more preferably from about 20-60% by weight, most preferably from about 30-50% by weight, in each case based on the weight of the blonding agent.

According to a particularly preferred embodiment of the present disclosure, the inorganic salt of a peroxosulfuric acid constitutes a mixture comprising from about 5 to about 40% by weight, preferably from about 10 to about 35% by weight, more preferably from about 15 to about 30% by weight of potassium peroxodisulfate, from about 5 to about 20% by weight, preferably from about 8 to about 18% by weight, more preferably from about 10 to about 15% by weight of ammonium peroxodisulfate and/or from about 2 to about 20% by weight, preferably from about 4 to about 15% by weight, more preferably from about 5 to about 10% by weight of sodium perooxodisulfate, in each case based on the total weight of the blonding agent.

According to a further preferred embodiment, the ratio of the amount of percarbonate to the total amount of persulfate(s) is between from about 2 to about 1 and from about 1 to about 20, preferably between from about 1 to about 1 and from about 1 to about 10, more preferably between from about 1 to about 2 and from about 1 to about 8, most preferably between from about 1 to about 3 and from about 1 to about 6.

According to a further preferred embodiment, the weight ratio of the amount of percarbonate to the total amount of persulfate(s) is between from about 2 to about 1 and from about 1 to about 20, preferably between from about 1 to about 1 and from about 1 to about 10, more preferably between from about 1 to about 2 and from about 1 to about 8, most preferably between from about 1 to about 3 and from about 1 to about 6.

In a particularly preferred embodiment, the percarbonate and the persulfate(s) are provided separately from one another. This can be accomplished by providing two separate pouches wherein the percarbonate is provided together with the sodium chloride and optionally other substances in one pouch and the persulfate is provided in a second pouch.

Blonding powders preferred as contemplated herein additionally contain at least one inorganic alkalizing agent which is solid at 20° C. and 1013 mbar, including at least one sodium silicate or sodium metasilicate having a molar $SiO_2/Na_2O$ ratio of ≥2, preferably from about 2.5-3.5 in a total amount of from about 0.1 to about 50% by weight, preferably from about 5 to about 40% by weight, in each case based on the weight of blonding powder.

Blonding powders preferred as contemplated herein contain at least one inorganic alkalizing agent solid at 20° C. and 1013 mbar, preferably in a total amount of from about 1-60% by weight, preferably from about 5-55% by weight, particularly preferably from about 10-50% by weight, most preferably from about 15-45% by weight, in each case based on the weight of the blonding powder.

In addition to the at least one sodium silicate or sodium metasilicate having a molar $SiO_2/Na_2O$ ratio of ≥2, preferably from about 2.5-3.5, in a total amount of from about 0.1 to about 50% by weight, preferably from about 5 to about 40% by weight, in each case based on the weight of the blonding powder, inorganic alkalizing agents solid at 20° C. and 1013 mbar are selected from alkaline earth metal silicates, alkaline earth metal hydroxide carbonates, alkaline earth metal carbonates, alkaline earth metal metasilicates, alkali metal hydroxides, alkaline earth metal hydroxides, (earth) alkali metal phosphates and (earth) alkaline hydrogen phosphates, and mixtures of these substances are further particularly preferred as contemplated herein as an optional alkalizing agent. As contemplated herein particularly preferred inorganic alkalizing agents that are solid at 20° C. and 1013 mbar solid are, in addition to the at least one obligatory sodium silicate or sodium metasilicate, each having a molar $SiO_2/Na_2O$ ratio of ≥2, preferably from about 2.5 to about 3.5, selected from magnesium hydroxide carbonates and mixtures of these alkalizing agents. Magnesium hydroxide carbonates which are preferred as contemplated herein are those having the formula $MgCO_3.Mg(OH)_2.2H_2O$ and those having the formula $MgCO_3.Mg(OH)_2$. Magnesium hydroxide carbonate having the formula $MgCO_3.Mg(OH)_2$ is particularly preferred as contemplated herein.

Particularly preferred blonding powders as contemplated herein contain, in each case based on their total weight, from about 0.1 to about 50% by weight, preferably from about 5 to about 40% by weight, of sodium silicates having a molar $SiO_2/Na_2O$ ratio of ≥2, preferably from about 2.5 to about 3.5, and from about 2-20% by weight, preferably from about 5-15% by weight, particularly preferably from about 8-25% by weight of magnesium hydroxide carbonate as an inorganic alkalizing agent solid at 20° C. and 1013 mbar.

Blonding powders extremely preferred as contemplated herein contain, in each case based on their total weight, from about 0.1% to about 50% by weight, preferably from about 5% to about 40% by weight, of sodium silicates having a molar $SiO_2/Na_2O$ ratio of ≥2, preferably from about 2.5 to about 3.5, and from about 2 to about 20% by weight, preferably from about 5 to about 15% by weight, particularly preferably from about 10 to about 13% by weight of magnesium hydroxide carbonate having the formula $MgCO_3.Mg(OH)_2$ as an inorganic alkalizing agent solid at 20° C. and 1013 mbar.

If the blonding powder as contemplated herein or preferred as contemplated herein contains one or more inorganic carbonates, be it as an alkalizing agent or as an oxidizing agent in the form of sodium carbonate-hydrogen peroxide complexes, their content is preferably selected such that in the application mixture with the oxidation composition (Ox) discussed below, the molar $CO_3^2$ total concentration is at least about 0.015 mol/100 grams of application mixture.

If the blonding powder as contemplated herein or preferred as contemplated herein contains one or more inorganic carbonates, be it as an alkalizing agent or as an oxidizing agent in the form of sodium carbonate-hydrogen peroxide complexes, their content is particularly preferably selected such that in the application mixture with the oxidation composition (Ox) discussed below, the total molar $CO_3^2$ concentration is mathematically at least four times higher than the total concentration of proton donors.

If the blonding powder as contemplated herein or preferred as contemplated herein contains one or more inorganic carbonates, either as an alkalizing agent or as an oxidizing agent in the form of sodium carbonate-hydrogen peroxide complexes, their content is extremely preferably selected such that in the application mixture with the oxidation composition (Ox) discussed below, the molar $CO_3^2$ total concentration is at least about 0.015 mol/100 grams of application mixture and is mathematically at least four times higher than the total concentrations of proton donors.

Preferred blonding agents additionally comprise at least one dicarboxylic acid having from about 2 to about 10 carbon atoms which is preferably selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, and/or at least one salt of these acids, particularly preferably in a total amount converted to the mass of free dicarboxylic acid of from about 0.03-7% by weight, preferably from about 0.1-5% by weight, particularly preferably from about 0.5-3% by weight, most preferably from about 0.9-1.5% by weight, in each case based on the weight of blonding agent.

Preferred blonding agents contain at least one amino acid which is selected from arginine, lysine, histidine or at least one salt of these amino acids, in a total amount converted to the mass of free amino acid of from about 0.1-7% by weight, preferably from about 0.2-5% by weight, particularly preferably from about 0.5-2.5% by weight, most preferably from about 1-2% by weight, in each case based on the weight of blonding agent.

Preferred blonding agents comprise at least one oil in a total amount of from about 0.1-80% by weight, preferably from about 2-60% by weight, more preferably from about 5-40% by weight, most preferably from about 10-35% by weight, in each case based on the weight of the blonding agent.

A suitable parameter for the quantification of fiber damage, in particular hair damage, is, for example, the measurement of the tensile strength (Young's modulus) of the keratinic fibers.

Salts of the dicarboxylic acids having from about 2 to about 10 carbon atoms which are preferred as contemplated herein are selected from the mono- and disalts of the anions of succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid and oxaloacetic acid with ammonium ions, alkali metal ions, alkaline earth metal ions and the ions of basic amino acids such as arginine, lysine and histidine, in particular with lithium, sodium, potassium, magnesium and calcium ions, and mixtures of these salts.

Particularly preferred succinic acid as contemplated herein has a melting point in the range from about 185-187° C. at 1013 mbar, that is, it is a solid at 20° C. Salts of succinic acid suitable as contemplated herein are selected from the succinates and hydrogen succinates of ammonium ions, alkali metal ions, alkaline earth metal ions and the ions of basic amino acids, such as arginine, lysine and histidine, in particular the lithium, sodium, potassium, magnesium and calcium ions, or the succinates and hydrogen succinates of basic amino acids, such as arginine, lysine and/or histidine, for example, arginine succinate, and mixtures of these salts. Said salts of succinic acid can also contain bound water of crystallization, in particular sodium succinate hexahydrate, which is particularly preferred as contemplated herein.

Particularly preferred malic acid as contemplated herein is optically active. Racemic DL-malic acid has a melting point in the range from about 131-132° C. at 1013 mbar, that is, it is a solid at 20° C. The enantiomers D-malic acid and L-malic acid each have a melting point in the range of from about 100-101° C. at 1013 mbar. Racemic DL-malic acid is preferred for cost reasons.

Salts of malic acid suitable as contemplated herein are selected from the malates and hydrogen malates of ammonium ions, alkali metal ions, alkaline earth metal ions and the ions of basic amino acids, such as arginine, lysine and histidine, in particular of lithium, sodium and potassium, magnesium and calcium ions, and mixtures of these salts, in particular disodium malate and dipotassium malate, but also calcium malate. Said salts of malic acid suitable as contemplated herein can contain bound water of crystallization, in particular disodium malate hemihydrate and disodium malate trihydrate.

Preferred oxalic acid as contemplated herein has a melting point of about 189.5° C. (anhydrous) at 1013 mbar or a melting point of about 101.5° C. as the dihydrate. Salts of oxalic acid suitable as contemplated herein are selected from the oxalates and hydrogen oxalates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred malonic acid as contemplated herein has a melting point of about 135° C. at 1013 mbar. Salts of malonic acid suitable as contemplated herein are selected from the malates and hydrogen malates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred adipic acid as contemplated herein has a melting point of about 152° C. at 1013 mbar. Salts of adipic acid suitable as contemplated herein are selected from the adipates and hydrogen adipates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred pimelic acid as contemplated herein has a melting point of about 105° C. at 1013 mbar. Salts of pimelic acid suitable as contemplated herein are selected from the pimelates and hydrogen pimelates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred suberic acid as contemplated herein has a melting point of about 144° C. at 1013 mbar. Salts of suberic acid suitable as contemplated herein are selected from the suberates and hydrogen suberates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred azelaic acid as contemplated herein has a melting point of about 106° C. at 1013 mbar. Salts of azelaic acid suitable as contemplated herein are selected from the azelates and hydrogen azelates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Preferred sebacic acid as contemplated herein has a melting point of about 134.5° C. at 1013 mbar. Salts of sebacic acid suitable as contemplated herein are selected from the sebacates and hydrogen sebacates of ammonium ions, alkali metal ions, alkaline earth metal ions and the ions of basic amino acids, such as arginine, lysine and histidine, in particular of lithium, sodium, potassium, magnesium and calcium ions, and mixtures of these salts.

Maleic acid particularly preferred as contemplated herein has, at 1013 mbar, a melting point of about 130 to about 131° C. (from ethanol or benzene) and from about 138 to about 139° C. (from water). Salts of maleic acid suitable as contemplated herein are selected from the maleates and hydrogen maleates of ammonium ions, alkali metal ions and alkaline earth metal ions, in particular of lithium, sodium, potassium, magnesium and calcium ions, and mixtures of these salts.

The fumaric acid particularly preferred as contemplated herein has a melting point of about 287° C. in the sealed tube at 1013 mbar; at 200° C., fumaric acid sublimes. Salts of fumaric acid suitable as contemplated herein are selected from the fumarates and hydrogen fumarates of ammonium ions, alkali metal ions and alkaline earth metal ions, in particular of lithium, sodium, potassium, magnesium and calcium ions, and mixtures of these salts.

Particularly preferred D-tartaric acid (levorotatory) as contemplated herein has a melting point of from about 168-170° C. at 1013 mbar. Salts of D-tartaric acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Particularly preferred L-tartaric acid (dextrorotatory) as contemplated herein has a melting point of from about 168-170° C. at 1013 mbar. Salts of L-tartaric acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Meso-tartaric acid particularly preferred as contemplated herein has a melting point of about 140° C. at 1013 mbar. Salts of meso-tartaric acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Particularly preferred racemic acid as contemplated herein is the racemic mixture of D-tartaric acid and L-tartaric acid. Racemic acid has a melting point of about 206° C. at 1013 mbar. Salts of racemic acid suitable as contemplated herein are selected from the tartrates and hydrogen tartrates of ammonium ions, alkali metal ions and alkaline earth metal ions, in particular of lithium, sodium, potassium, magnesium and calcium ions, and mixtures of these salts.

Particularly preferred alpha-ketoglutaric acid as contemplated herein has a melting point of from about 112-116° C. at 1013 mbar. Salts of alpha-ketoglutaric acid suitable as contemplated herein are selected from the alpha-ketoglutarates and alpha-ketohydrogen glutarates of ammonium ions, alkali metal ions and alkaline earth metal ions, in particular of lithium, sodium, potassium, magnesium and calcium ions, and mixtures of these salts.

Particularly preferred beta-ketoglutaric acid as contemplated herein has a melting point of about 122° C. at 1013 mbar; it melts with decomposition. Salts of beta-ketoglutaric acid suitable as contemplated herein are selected from the beta-ketoglutarates and beta-ketohydrogen glutarates of ammonium ions, alkali metal ions and alkaline earth metal ions, in particular of lithium, sodium, potassium, magnesium and calcium ions, and mixtures of these salts.

Particularly preferred oxaloacetic acid as contemplated herein has a melting point of about 161° C. at 1013 mbar. Salts of oxalacetic acid suitable as contemplated herein are selected from the oxalacetates and oxalhydrogen acetates of ammonium ions, alkali metal ions and alkaline earth metal ions, in particular of lithium, sodium, potassium, magnesium and calcium ions, and mixtures of these salts.

Blonding powders preferred as contemplated herein contain the at least one dicarboxylic acid having from about 2 to about 10 carbon atoms, selected from succinic acid, malic acid, oxalic acid, malonic acid, adipic acid, pimelic acid, suberic acid, azelaic acid, sebacic acid and/or at least one salt of these acids, in a total amount converted to the mass of free dicarboxylic acid of from about 0.03-7% by weight, preferably from about 0.1-5% by weight, particularly preferably from about 0.5-3% by weight, most preferably from about 0.9-1.5% by weight, in each case based on the weight of blonding powder.

Further blonding powders preferred as contemplated herein contain succinic acid and/or at least one salt of succinic acid in a total amount converted to the mass of free dicarboxylic acid of from about 0.03-7% by weight, preferably from about 0.1-5% by weight, particularly preferably from about 0.5-3% by weight, exceptionally preferably from about 0.9-1.5% by weight, in each case based on the weight of the blonding powder.

Further blonding powders preferred as contemplated herein contain malic acid and/or at least one salt of malic acid in a total amount converted to the mass of free dicarboxylic acid of from about 0.03-7% by weight, preferably from about 0.1-5% by weight, particularly preferably from about 0.5-3% by weight, exceptionally preferably from about 0.9-1.5% by weight, in each case based on the weight of the blonding powder.

For dedusting the blonding powder as contemplated herein, at least one dedusting agent can be added which is in particular selected from at least one oil, in particular selected from paraffin oil, silicone oil or ester oil and mixtures of these oils.

Blonding powders preferred as contemplated herein therefore additionally contain at least one oil in a total amount of from about 0.1-15% by weight, preferably from about 0.5-10% by weight, more preferably from about 1-8% by weight, most preferably from about 2-6% by weight, in each case based on the weight of blonding powder.

Oils preferred as contemplated herein are selected from natural and synthetic hydrocarbons, more preferably from paraffin oils, $C_{18}$-$C_{30}$ isoparaffins, in particular isoeicosane, polyisobutenes and polydecenes, furthermore selected from $C_8$-$C_{16}$ isoparaffins, in particular from isodecane, isododecane, isotetradecane and Isohexadecane and mixtures thereof, and 1,3-di-(2-ethylhexyl) cyclohexane.

Further preferred oils as contemplated herein are selected from the benzoic acid esters of linear or branched C8-22 alkanols. Particularly preferred are benzoic acid C12-C15 alkyl esters.

Further preferred oils are selected from fatty alcohols having from about 6-30 carbon atoms which are unsaturated or branched and saturated or branched and unsaturated. Preferred alcohol oils are 2-hexyldecanol, 2-octyldodecanol, 2-ethylhexyl alcohol and isostearyl alcohol.

Further preferred oils as contemplated herein are selected from the triglycerides (=triple esters of glycerol) of linear or branched, saturated or unsaturated, optionally hydroxylated C8-30 fatty acids. Particularly preferred can be the use of natural oils, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderflower seed oil, currant seed oil, jojoba oil, linseed oil, macadamia nut oil, corn oil, almond oil, Marula oil, evening primrose oil, olive oil, palm oil, palm kernel oil, Brazil nut oil, pecan oil, peach kernel oil, rapeseed oil, castor oil, sea buckthorn fruit oil, sea buckthorn seed oil, sesame oil, soybean oil, sunflower oil, grapeseed oil, walnut oil, wild rose oil, wheat germ oil, and the liquid portions of coconut oil and the like. However, synthetic triglyceride oils are also preferred, in particular Capric/Caprylic Triglycerides.

Further preferred oils as contemplated herein are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further particularly preferred cosmetic oils as contemplated herein are selected from the esters of linear or branched saturated or unsaturated fatty alcohols having from about 2-30 carbon atoms with linear or branched saturated or unsaturated fatty acids having from about 2 to about 30 carbon atoms which can be hydroxylated. These preferably include 2-hexyldecyl stearate, 2-hexyldecyl laurate, isodecyl neopentanoate, isononyl isononanoate, 2-ethylhexyl palmitate and 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyl dodecyl palmitate, butyloctanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate and ethylene glycol dipalmitate.

Further preferred cosmetic oils as contemplated herein are selected from the addition products of 1 to 5 propylene oxide units of mono- or multivalent $C_8$-$C_{22}$ alkanols such as octanol, decanol, decanediol, lauryl alcohol, myristyl alcohol and stearyl alcohol, for example, PPG-2 myristyl ether and PPG-3 myristyl ether. Further preferred cosmetic oils as contemplated herein are selected from the addition products of at least 6 ethylene oxide and/or propylene oxide units of monovalent or polyvalent $C_3$-22 alkanols such as glycerol, butanol, butanediol, myristyl alcohol and stearyl alcohol, which can be esterified if desired, for example, PPG-14 butyl ether, PPG-9-butyl ether, PPG-10-butanediol, PPG-15 stearyl ether and glycereth-7-diisononanoate.

Further preferred cosmetic oils as contemplated herein are selected from the $C_8$-$C_{22}$ fatty alcohol esters of monovalent or multivalent $C_2$-$C_7$ hydroxycarboxylic acids, in particular the esters of glycolic acid, lactic acid, malic acid, tartaric acid, citric acid and salicylic acid, for example, $C_{12}$-$C_{15}$ alkyl lactate.

Further preferred cosmetic oils as contemplated herein are selected from the symmetrical, asymmetric or cyclic esters of carbonic acid with $C_{3-22}$ alkanols, $C_{3-22}$ alkanediols or $C_{3-22}$ alkanetriols, for example, dicaprylyl carbonate, or the esters according to DE 19756454 A1, in particular glycerol carbonate.

Further cosmetic oils as contemplated herein which are suitable are selected from silicone oils including, for example, dialkyl and alkylaryl siloxanes such as decamethylcyclopentasiloxane, dodecamethylcyclohexasiloxane, dimethylpolysiloxane and methylphenylpolysiloxane, but also hexamethyldisiloxane, octamethyltrisiloxane and decamethyltetrasiloxane.

It can be extremely preferable according to the present disclosure to use mixtures of the aforementioned oils.

Preferred blonding powders as contemplated herein include cosmetic oil that is selected from natural and synthetic hydrocarbons, more preferably from paraffin oils, $C_{18}$-$C_{30}$ isoparaffins, in particular isoeicosane, polyisobutenes and polydecenes, $C_8$-$C_{16}$ isoparaffins, and 1,3-di-(2-ethylhexyl) cyclohexane; the benzoic acid esters of linear or branched $C_{8-22}$ alkanols; fatty alcohols having from about 6-30 carbon atoms which are unsaturated or branched and saturated or branched and unsaturated; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched saturated or unsaturated fatty alcohols having from about 2-30 carbon atoms with linear or branched saturated or unsaturated fatty acids having from about 2-30 carbon atoms which can be hydroxylated; the addition products of 1 to 5 propylene oxide units of monovalent or polyvalent $C_{8-22}$ alkanols; the addition products of at least 6 ethylene oxide and/or propylene oxide units of monovalent or polyvalent $C_{3-22}$ alkanols; $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the aforementioned substances and preferably is present in a total amount of from about 0.1-15% by weight, preferably from about 0.5-10% by weight, particularly preferably from about 1-8% by weight, most preferably from about 2-6% by weight, in each case based on the weight of blonding powder.

Further preferred blonding powders as contemplated herein contain at least one polymer selected from acrylic acid homopolymers and copolymers, methacrylic acid homopolymers and copolymers, itaconic acid homopolymers and copolymers, polysaccharides, which can be chemically and/or physically modified, and mixtures of these polymers, wherein particularly preferably one or more of said polymers is present in a total amount of from about 0.1-6% by weight, preferably from about 0.5-4% by weight, particularly preferably from about 1-3.5% by weight, most preferably from about 2-3% by weight, in each case based on the weight of blonding powder.

The object underlying the present disclosure is further achieved by a method for the lightening of keratinic fibers. A further subject of the present disclosure therefore relates to a method for lightening keratinic fibers, in particular human hair. The method for lightening keratinic fibers, in particular human hair, is exemplified in that a blonding agent (B) according to the first subject of the present disclosure is mixed with water, applied immediately afterwards to the keratin-containing fibers, left on the fibers for from about 5 to about 60 minutes and then the fibers are rinsed with water and optionally washed with a surfactant-containing cleaning agent. According to a preferred embodiment, the blonding agent and water are blended in a weight-blending ratio of blonding agent to water of from about 1 to about 1 to about 1 to about 5, more preferably from about 1 to about 1 to about 1 to about 4, most preferably from about 1 to about 1 to about 1 to about 3.

The agent used as the oxidation composition in the lightening method as contemplated herein consists substantially of water. The term "consists substantially of water" means as contemplated herein a water content of from about 80 to about 100% by weight, preferably from about 90 to about 100% by weight, particularly preferably from about 97-100% by weight of water, in each case based on the weight of the agent used as the oxidation composition. The water is used in the context of the present disclosure as an oxidation composition or should be referred to as such. In conventional methods for brightening keratinic fibers, in particular human hair, the oxidation composition contains hydrogen peroxide. In the case of the present disclosure, however, hydrogen peroxide in liquid or dissolved form should be dispensed with. The percarbonate forms the oxidizing species by using the water. Therefore, the water or water-containing solution which is free from hydrogen peroxide should be referred to as the oxidation composition. The water or water-containing solution makes the blonding agent the ready-to-use oxidation composition.

As contemplated herein, the blonding powder is preferably composed such that the mixture with the aforementioned oxidation composition (Ox) substantially comprises water, that is, the ready-to-use color-changing agent, in particular blonding agent, has an alkaline pH value, preferably a pH value of from about 8 to about 11.5, particularly preferably a pH value of from about 8.5 to about 11, most preferably a pH value of from about 9.0 to about 10.5, each measured at 20° C.

Oxidation compositions (Ox) used particularly preferably as contemplated herein furthermore contain at least one oil and/or at least one fatty component having a melting point in the range of from about 23-110° C., preferably in a total amount of from about 0.1-60% by weight, particularly preferably from about 0.5-40% by weight, most preferably from about 2-24% by weight, in each case based on the weight of the preferably used oxidation composition (Ox) as contemplated herein. The oils suitable for the oxidation compositions (Ox) preferably used as contemplated herein are the same oils which are disclosed above as suitable dedusting agents.

Fatty components having a melting point in the range of from about 23-110° C. preferably used in the oxidation compositions (Ox) as contemplated herein are selected from linear saturated 1-alkanols having 12-30 carbon atoms, preferably in a total amount of from about 0.1-8% by weight, particularly preferably from about 3.0 to about 6.0% by weight, in each case based on the weight of the oxidation composition (Ox) used as contemplated herein.

Preferably, the at least one linear saturated 1-alkanol having from about 12-30 carbon atoms is selected from lauryl alcohol, myristyl alcohol, cetyl alcohol, stearyl alcohol, arachidyl alcohol, and behenyl and from mixtures of these 1-alkanols, more preferably from cetyl alcohol, stearyl alcohol and cetyl alcohol/stearyl alcohol mixtures.

Oxidation compositions (Ox) preferably used as contemplated herein furthermore contain, in each case based on their weight, at least one linear saturated 1-alkanol having from about 12-30 carbon atoms is present in a total amount of from about 0.1-8% by weight, preferably in a total amount of about 2.6% by weight, wherein at least one 1-alkanol selected from cetyl alcohol, stearyl alcohol and cetyl alcohol/stearyl alcohol mixtures.

Further oxidation compositions (Ox) preferably used as contemplated herein contain at least one fatty component having a melting point in the range of from about 23-110° C., which is selected from esters of a saturated, monovalent $C_{16}$-$C_{60}$-alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids which can be hydroxylated, candelilla wax, carnauba wax, beeswax, saturated linear $C_{14}$-$C_{36}$ carboxylic acids and mixtures of the aforementioned substances.

Further oxidation compositions (Ox) preferably used as contemplated herein contain at least one surfactant or at least one emulsifier, preferably in a total amount of from about 0.5-10% by weight, preferably from about 1-5% by weight, in each case based on the weight oxidation composition (Ox) used as contemplated herein.

Surfactants and emulsifiers in the context of the present application are amphiphilic (bifunctional) compounds which include at least one hydrophobic and at least one hydrophilic molecule part. The hydrophobic radical is preferably a hydrocarbon chain having from about 8-28 carbon atoms, which can be saturated or unsaturated, linear or branched. Particularly preferably, this $C_8$-$C_{28}$ alkyl chain is linear. Basic properties of the surfactants and emulsifiers are the oriented absorption at interfaces and the aggregation to micelles and the formation of lyotropic phases.

Anionic, nonionic and cationic surfactants are particularly suitable as contemplated herein. However, zwitterionic and amphoteric surfactants are also very suitable as contemplated herein.

All anionic surfactants suitable for use on the human body are suitable as anionic surfactants in the compositions as contemplated herein. These are exemplified by a water-solubilizing, anionic group such as a carboxylate, sulfate, sulfonate or phosphate group and a lipophilic alkyl group having from about 8 to about 30 carbon atoms. In addition, glycol or polyglycol ether groups, ester, ether and amide groups and hydroxyl groups can be present in the molecule. Examples of suitable anionic surfactants are linear and branched fatty acids containing from about 8 to 30 carbon atoms (soaps), alkyl ether carboxylic acids, acylsarcosides, acyl taurides, acyl isethionates, sulfosuccinic acid mono and dialkyl esters, sulfosuccinic acid monoalkyl polyoxyethyl esters, linear alkanesulfonates, linear alpha-olefinsulfonates, alkyl sulfates and alkyl ether sulfates and alkyl and/or alkenyl phosphates. Preferred anionic surfactants are alkyl sulfates, alkyl ether sulfates and alkyl ether carboxylic acids having in each case from about 10 to about 18 C atoms, preferably 12 to 14 C atoms in the alkyl group and up to 12 glycol ether groups, preferably from about 2 to about 6 glycol ether groups in the molecule. Examples of such surfactants are the compounds with the INCI names Sodium Laureth Sulfate, Sodium Lauryl Sulfate, Sodium Myreth Sulfate or Sodium Laureth Carboxylate.

Zwitterionic surfactants are surface-active compounds which carry at least one quaternary ammonium group and at least one carboxylate, sulfonate or sulfate group in the molecule. Particularly suitable zwitterionic surfactants are the so-called betaines such as N-alkyl-N,N-dimethylammonium glycinates, for example, cocoalkyl dimethylammonium glycinate, N-acylaminopropyl N,N-dimethylammonium glycinates, for example, cocoacylaminopropyl-dimethylammonium glycinate, and 2-alkyl-3-carboxymethyl-3-hydroxyethyl-imidazolines each having from about 8 to about 18 carbon atoms in the alkyl or acyl group and cocoacylamino ethyl hydroxyethyl carboxymethyl glycine. A preferred zwitterionic surfactant is the fatty acid amide derivative known by the INCI name Cocamidopropyl Betaine.

Amphoteric surfactants are understood to mean those surface-active compounds which, apart from a $C_8$-$C_{24}$ alkyl or acyl group in the molecule, contain at least one free amino group and at least one —COOH or —$SO_3H$ group and which are capable of forming internal salts. Examples of suitable amphoteric surfactants are N-alkylglycines, N-alkylpropionic acids, N-alkylaminobutyric acids, N-alkylimino-dipropionic acids, N-hydroxyethyl-N-alkylamidopropylglycine, N-alkyltaurines, N-alkylsarcosines, 2-alkylaminopropionic acids and alkylaminoacetic acids, each having from about 8 to about 24 carbon atoms in the alkyl group. Particularly preferred amphoteric surfactants are N-coco alkylamine propionate and $C_{12}$-$C_{18}$ acylsarcosine.

Nonionic surfactants contain as hydrophilic group, for example, a polyol group, a polyalkylene glycol ether group or a combination of polyol and polyglycol ether groups. Such compounds are, for example, addition products of from about 4 to about 50 moles of ethylene oxide and/or from 0 to about 5 moles of propylene oxide with linear and branched fatty alcohols, on fatty acids and on alkylphenols, each having from about 8 to about 20 carbon atoms in the alkyl group, ethoxylated mono-, di- and triglycerides, such as glycerol monolaurate+20 ethylene oxide, and glycerol monostearate+20 ethylene oxide, sorbitan fatty acid esters and addition products of ethylene oxide on sorbitan fatty acid esters such as the polysorbates (Tween 20, Tween 21, Tween 60, Tween 61, Tween 81), addition products of ethylene oxide on fatty acid alkanolamides and fatty amines, and alkylpolyglycosides. Suitable nonionic surfactants are, in particular, $C_8$-$C_{22}$ alkyl mono- and -oligoglycosides and their ethoxylated analogs and ethylene oxide addition products on saturated or unsaturated linear fatty alcohols with from about 2 to about 30 mole of ethylene oxide per mole of fatty alcohol.

Further oxidation compositions preferably used as contemplated herein include at least one anionic surfactant that is selected from alkyl sulfates, alkyl ether sulfates and alkyl ether carboxylic acids, each having from about 10 to about 18 C atoms, preferably 12 to 14 C atoms in the alkyl group and up to 12, preferably from about 2 to about 6 glycol ether groups, in the molecule.

Further oxidation compositions preferably used as contemplated herein are exemplified in that at least one nonionic surfactant selected from ethylene oxide addition products of saturated or unsaturated linear fatty alcohols each with from about 2 to about 30 moles of ethylene oxide per mole of fatty alcohol, and at least one anionic surfactant selected from alkyl sulfates, alkyl ether sulfates and alkyl ether carboxylic acids each having from about 10 to about 18 C atoms, preferably from 12 to 14 C atoms in the alkyl group and up to about 12, preferably from about 2 to about 6 glycol ether groups, is present in the molecule, wherein particularly preferred the weight ratio of the total of all anionic surfactants to the total of all nonionic surfactants is in the range of from about 5-50, preferably from about 10-30.

Suitable cationic surfactants in oxidation compositions (Ox) preferably used as contemplated herein are in principle all cationic surface-active substances suitable for use on the human body. These are exemplified by at least one water-solubilizing, cationic group, such as a quaternary ammonium group, or by at least one water-solubilizing, cationizable group such as an amine group, and further at least one (lipophilic-acting) alkyl group having from about 6 to about 30 carbon atoms or at least one (lipophilic-acting) imidazole group or at least one (lipophilic-acting) imidazylalkyl group.

Oxidation compositions (Ox) used particularly preferably as contemplated herein contain at least one cationic surfactant, which is preferably selected from quaternary ammonium compounds having at least one $C_8$-$C_{24}$ alkyl radical, esterquats and amidoamines each having at least one $C_8$-$C_{24}$ acyl radical and mixtures thereof. Preferred quaternary ammonium compounds having at least one $C_8$-$C_{24}$ alkyl radical are ammonium halides, in particular chlorides, and ammonium alkyl sulfates, such as methosulfates or ethosulfates, such as $C_8$-$C_{24}$ alkyltrimethylammonium chlorides, $C_8$-$C_{24}$ dialkyldimethylammonium chlorides and $C_8$-$C_{24}$ trialkylmethylammonium chlorides, for example, cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27, Quaternium-83, Quaternium-87 and Quaternium-91. The alkyl chains of the above-mentioned surfactants preferably have from about 8 to about 24 carbon atoms.

Esterquats are cationic surfactants which contain both at least one ester function and at least one quaternary ammonium group as a structural element and furthermore at least one $C_8$-$C_{24}$ alkyl radical or $C_8$-$C_{24}$ acyl radical. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trademarks Stepantex®, Dehyquart® and Armocare®. N,N-bis(2-palmitoyloxyethyl) dimethylammonium chloride, distearoylethyl dimonium methosulfate and distearoylethyl hydroxyethylmonium methosulfate are preferred examples of such ester quats.

The alkylamidoamines are usually prepared by amidation of natural or synthetic $C_8$-$C_{24}$ fatty acids and fatty acid cuts with di ($C_1$-$C_3$) alkylaminoamines. A particularly suitable compound of this substance group as contemplated herein is stearamidopropyldimethylamine.

Oxidation compositions (Ox) used particularly preferably as contemplated herein contain at least one cationic surfactant in a total amount of from about 0.01-5% by weight, preferably from about 0.1-3% by weight, particularly preferably from about 0.3-2% by weight, in each case based on the weight of the oxidation composition (Ox) used as contemplated herein.

A further object of the present disclosure is a multi-component packaging unit (kit-of-parts) for lightening keratinic fibers containing at least two components separately packaged and which is exemplified in that
i) the first component (I) is a blonding powder as contemplated herein or a preferred blonding powder as contemplated herein,
ii) the second component (II) is substantially water or an aqueous solution.

A further object of the present disclosure is a multi-component packaging unit (kit-of-parts) for color change of keratinic fibers, in particular human hair, containing at least three separately packaged components, which is exemplified in that
i) the first component (I) is a blonding agent as contemplated herein or a preferred blonding agent as contemplated herein,
ii) the second component (II) contains from about 80 to 100% by weight, preferably from about 90 to 100% by weight, particularly preferably from about 97 to 100% by weight of water, in each case based on the weight of component (II),
iii) the third component (III) is an alkalization composition (Alk) containing water and at least one alkalizing agent selected from ammonia, alkanolamines and mixtures thereof and having a pH value in the range of from about 8-12, preferably from about 9-11, more preferably from about 9.5-10.5, each measured at 20° C.,
wherein neither component (II) nor component (III) contain hydrogen peroxide.

The aforementioned multi-component packaging unit is particularly preferred when component (II) has a pH value in the range of from about 6.5-8.0, preferably from about 6.8-7.5, particularly preferably from about 7.0-7.2, each measured at 20° C.

A further object of the present disclosure is a multi-component packaging unit (kit-of-parts) for color change of keratinic fibers, in particular human hair, containing at least three separately packaged components, which is exemplified in that
i) the first component (I) is a blonding agent as contemplated herein or a preferred blonding agent as contemplated herein,
ii) the second component (II) is substantially water and has a pH value in the range of from about 2.5 to about 5.5, measured at 20° C.,
iii) the third component (III) is an alkalization composition (Alk) containing water and at least one alkalizing agent selected from ammonia, alkanolamines and mixtures thereof and having a pH value in the range of from about 8-12, preferably from about 9-11, more preferably from about 9.5-10.5, each measured at 20° C.

A multi-component packaging unit comprises a plurality of individual components, which are assembled separately from one another, and a common packaging for these components, for example, a folding box. The components are each provided separately in different containers therein. In the context of the present disclosure, container is understood to mean a casing which is present in the form of an optionally reclosable bottle, a tube, a can, a sachet or a similar wrapping. There are no limits for wrapping material as contemplated herein. However, these are preferably casings made of glass or plastic.

In addition, the packaging unit can comprise application aids, such as combs, brushes, personal protective clothing, in particular disposable gloves, and instructions for use.

In a further preferred embodiment as contemplated herein, a blonding powder as contemplated herein or a preferred blonding powder as contemplated herein having an alkalization composition and having an oxidation composition can be combined to form a lightening color-changing agent for keratinic fibers.

Since, in the treatment of keratinic fibers, in particular hair, with oxidizing agents, the fibrous dye melanin is destroyed to some degree, the fibers/hair are inevitably lightened, thus changing their color even without the presence of a dye. Therefore, the term "color change" in the context of the present application encompasses both lightening and staining with one or more dyes.

The alkalization composition (Alk) used as contemplated herein contains water and at least one alkalizing agent selected from ammonia, alkanolamines and mixtures thereof, and has a pH value in the range of from about 8-12, preferably from about 9-11, more preferably from about 9.5-10.5, each measured at 20° C. Preferred alkanolamines are selected from monoethanolamine, 2-amino-2-methyl-propanol and triethanolamine and mixtures thereof, wherein monoethanolamine is particularly preferred. An extraordinarily preferred alkalizing agent is ammonia.

Usually, ammonia ($NH_3$) is used in the form of its aqueous solution. Aqueous ammonia solutions often contain ammonia ($NH_3$) in concentrations of from about 10 to about 32% by weight. Preference is given to the use of an aqueous ammonia solution containing about 25% by weight ammonia ($NH_3$).

In addition to ammonia and alkanolamines, at least one further alkalizing agent can be present, which is selected from alkali metal silicates, alkaline earth metal silicates, alkaline earth metal hydroxide carbonates, alkaline earth metal carbonates, alkali metal metasilicates, alkaline earth metal metasilicates, alkali metal hydroxides and alkaline earth metal hydroxides, and mixtures of these substances.

Ammonia and/or monoethanolamine preferred in the alkalization compositions preferably used as contemplated herein are present in amounts of from about 0.01-10% by weight, preferably from about 0.1-7.5% by weight, more preferably from about 0.5-5.5% by weight and particularly preferably from about 1.5 to about 4.5% by weight, in each case based on the weight of the alkalization composition.

As contemplated herein, the blonding powder is preferably composed such that the mixture with the aforementioned oxidation composition (Ox) and with the aforementioned alkalization composition (Alk), that is, the ready-to-use color-changing agent, in particular blonding agent, has an alkaline pH value, preferably a pH value of from about 8 to about 11.5, particularly preferably a pH value of from about 8.5 to about 11, most preferably a pH value of from about 9.0 to about 10.5, each measured at 20° C.

The ready-to-use mixtures of a blonding powder as contemplated herein or preferred as contemplated herein with one of the aforementioned oxidation compositions (Ox) and optionally with one of the aforementioned alkalization compositions (Alk) preferably have a viscosity in the range from about 15,000 to about 100,000 mPas, particularly preferably from about 20,000 to about 85,000 mPas, respectively measured at 20° C. with a Brookfield viscometer type DV-II+, spindle 5 at a speed of 4 revolutions/minute. A viscosity in this range allows the ready-to-use cosmetic agent to be well applied on the one hand and have a flow behavior on the other hand to ensure that the agent has a sufficiently long exposure time on the keratinic fibers at the site of action.

In order to facilitate the miscibility of the alkalization composition used as contemplated herein with the blonding agent as contemplated herein or preferred blonding agent as contemplated herein and the oxidizing composition as contemplated herein and to improve the application properties of the resulting use mixture, the alkalization composition preferably used as contemplated herein preferably contains at least one surfactant in a total amount, based on its weight, from about 0.5-10% by weight, preferably from about 2-8% by weight.

The surfactants suitable for the alkalization compositions (Alk) preferably used as contemplated herein are selected from the same anionic, cationic, nonionic, amphoteric and zwitterionic surfactants and emulsifiers which are disclosed above as surfactants and emulsifiers suitable for the preferred used oxidation compositions (Ox).

Oxidation compositions (Ox) used particularly preferably as contemplated herein furthermore contain at least one oil and/or at least one fatty component having a melting point in the range of from about 23-110° C., preferably in a total amount of from about 0.1-60% by weight, particularly preferably from about 0.5-40% by weight, most preferably from about 2-24% by weight, in each case based on the weight of the preferably used alkalization composition (Alk) as contemplated herein. The oils suitable for the alkalization compositions (Alk) preferably used as contemplated herein are the same oils which are disclosed above as suitable dedusting agents.

Fatty compounds having a melting point in the range of from about 23-110° C. preferably used in the alkalization compositions (Alk) as contemplated herein are preferably selected from linear saturated 1-alkanols having 12-30 carbon atoms, preferably in a total amount of from about 0.1-20% by weight, particularly preferably from about 3-15% by weight, most preferably from about 5-10% by weight, in each case based on the weight of the alkalization composition used in the present disclosure.

Preferably, the at least one linear saturated 1-alkanol having from about 12-30 carbon atoms is selected from lauryl alcohol, myristyl alcohol, cetyl alcohol, stearyl alcohol, arachidyl alcohol, and behenyl and from mixtures of these 1-alkanols, more preferably from cetyl alcohol, stearyl alcohol and cetyl alcohol/stearyl alcohol mixtures.

Alkalizing compositions (Alk) preferably used as contemplated herein furthermore contain, in each case based on their weight, at least one linear saturated 1-alkanol having from about 12-30 carbon atoms in a total amount of from about 0.1-20% by weight, preferably in a total amount of from about 3-15% by weight, exceptionally preferably from about 5 to 10% by weight, wherein at least one 1-alkanol selected from cetyl alcohol, stearyl alcohol and cetyl alcohol/stearyl alcohol mixtures is present.

Further alkalization compositions (Alk) preferably used as contemplated herein contain at least one fatty component having a melting point in the range of from about 23-110° C., which is selected from esters of a saturated, monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids which can be hydroxylated, candelilla wax, carnauba wax, beeswax, saturated linear $C_{14}$-$C_{36}$ carboxylic acids and mixtures of the aforementioned substances.

Furthermore, the blonding powders as contemplated herein or preferred as contemplated herein and/or the alkalization compositions preferably used as contemplated herein can contain at least one direct acting dye. These are dyes that are applied directly to the hair and do not require an oxidative process to form the color. For matting unwanted residual color impressions caused by melanin degradation products, in particular in the reddish or bluish range, particular direct acting dyes of the complementary colors are particularly preferred. Direct dyes are usually nitrophenylenediamines, nitroaminophenols, azo dyes, anthraquinones or indophenols. Direct dyes can be anionic, cationic or nonionic. The direct acting dyes are each preferably present in an amount of from about 0.001 to about 2% by weight, based on the weight of the blonding powder or the alkalization composition (Alk).

Preferred anionic direct acting dyes are those compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic direct acting dyes are cationic triphenylmethane dyes such as Basic Blue 7, Basic Blue 26, Basic Violet 2 and Basic Violet 14, aromatic systems which are substituted with a quaternary nitrogen group such as Basic Yellow 57, Basic Red 76, Basic Blue 99, Basic Brown 16 and Basic Brown 17, cationic anthraquinone dyes such as HC Blue 16 (Bluequat B) and direct acting dyes which contain a heterocycle having at least one quaternary nitrogen atom, in particular Basic Yellow 87, Basic Orange 31 and Basic Red 51. The cationic direct acting dyes that are sold under the trademark Arianor are also preferred cationic direct acting dyes as contemplated herein. In particular, nonionic nitro and quinone dyes and neutral azo dyes are suitable nonionic direct acting dyes. Preferred nonionic direct acting dyes are those compounds known under the international names or trade names Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)-amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol. Very particularly preferred as contemplated herein is a combination of tetrabromophenol blue and Acid Red 92.

In the case where persulfates are used, they are provided separately from the percarbonate and separately from the dye precursors.

As a further optional ingredient, the alkalization composition preferably used as contemplated herein contains at least one oxidation dye precursor, which is preferably selected from one or more developer components and optionally one or more coupler components.

Particularly preferably, at least one oxidation dye precursor is present in a total amount of from about 0.0001 to about 10.0% by weight, preferably from about 0.001 to about 8% by weight, in each case based on the weight of the alkalization composition preferably used as contemplated herein.

It can be preferred as contemplated herein to select as the developer component at least one compound from the group which is formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl] amine, N,N'-bis-(2-hydroxyethyl)-N,N'-bis-(4-aminophenyl)-1,3-diamino-propan-2-ol, bis-(2-hydroxy-5-aminophenyl) methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, and their physiologically compatible salts.

Particularly preferably, at least one developer component is present in a total amount of from about 0.0001 to about 10.0% by weight, preferably from about 0.001 to about 8% by weight, in each case based on the weight of the alkalization composition preferably used as contemplated herein.

Coupler components do not alone form significant dyeing in the context of oxidative dyeing, but always require the presence of developer components. Therefore, it is preferred as contemplated herein that at least one coupler component is additionally used when using at least one developer component.

Preferred coupler components as contemplated herein are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl) amino-2-methylphenol, 3-(diethylamino) phenol, N-cyclopentyl-3-aminophenol, 1,3-dihydroxy-5-(methylamino) benzene, 3-ethylamino-4-methylphenol, 2,4-dichloro-3-aminophenol, 2-(2,4-diaminophenoxy) ethanol, 1,3-bis (2,4-diaminophenoxy) propane, 1-methoxy-2-amino-4-(2-hydroxyethylamino) benzene, 1,3-bis-(2,4-diaminophenoxy) propane, 2,6-bis-(2'-hydroxyethylamino)-1-methylbenzene, 2-(13-[(2-hydroxyethyl) amino]-4-methoxy-5-methylphenyl) amino) ethanol, 2-({3-[(2-hydroxyethyl) amino]-2-methoxy-5-methylphenyl} amino) ethanol, 2-({3-[(2-hydroxyethyl) amino]-4,5-dimethylphenyl}amino) ethanol, 2-[3-morpholine-4-ylphenyl) amino] ethanol, 3-amino-4-(2-methoxyethoxy)-5-methylphenylamine, 1-amino-3-bis-(2-hydroxyethyl) aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxy ethyl) amino-3-amino-6-methoxypyridine, 2-(4'-methoxyphenyl) amino-3-amino-pyridine, 1-naphthol, 2-methyl-1-naphthol, 2-hydroxy methyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or their physiologically compatible salts.

Particularly preferably, at least one coupler component is present in a total amount of from about 0.0001 to about 10.0% by weight, preferably from about 0.001 to about 8% by weight, in each case based on the weight of the alkalization composition preferably used as contemplated herein.

In this case, developer components and coupler components are generally used in approximately equimolar amounts to each other. Although the equimolar use has proved to be expedient, a certain excess of individual oxidation dye precursors is not disadvantageous, so that developer components and coupler components can be present in a molar ratio of from about 0.2-2, in particular from about 0.5-1.

The exposure time is preferably from about 5 to about 60 minutes, in particular from about 5 to about 50 minutes, particularly preferably from about 10 to about 45 minutes. During the exposure time of the agents on the fiber, it can be advantageous to assist the whitening or color changing process by supplying heat. An exposure phase at room temperature is also as contemplated herein. In particular, the temperature during the exposure time lies between about 20° C. and about 40° C., in particular between about 25° C. and about 38° C. The agents yield good treatment results even at physiologically compatible temperatures of below about 45° C.

After the end of the color-changing operation, all components located on the keratinic fibers are rinsed out of the hair with water or a surfactant-containing cleaning agent. Commercial shampoo in particular can be used as a cleaning agent in this case, wherein in particular the cleaning agent can then be dispensed with and the rinsing process can be done with tap water when the color changing agent has a higher surfactant content.

A further object of the present disclosure is the use of a blonding agent according to the first aspect of the present disclosure for changing the natural color of keratinic fibers, in particular human hair, preferably for blonding or optical lightening of keratinic fibers, in particular human hair.

The statements made regarding the blonding powders as contemplated herein and preferred as contemplated herein also apply mutatis mutandis to the multi-component packaging units (kits of parts) as contemplated herein and preferably as contemplated herein.

The statements made regarding the blonding powders as contemplated herein and preferred as contemplated herein also apply mutatis mutandis to the methods for lightening and/or changing the color of the keratinic fibers as contemplated herein and preferred as contemplated herein.

The statements made regarding the oxidation compositions or alkalization compositions used as contemplated herein and preferred as contemplated herein also apply mutatis mutandis to the multi-component packaging units (kits of parts) as contemplated herein and preferably as contemplated herein.

The statements made regarding the oxidation compositions or alkalization compositions used as contemplated herein and preferred as contemplated herein also apply mutatis mutandis to the methods for lightening and/or changing the color of the keratinic fibers as contemplated herein and preferred as contemplated herein.

The statements made regarding the blonding powders as contemplated herein and preferred as contemplated herein also apply mutatis mutandis to the use as contemplated herein.

The statements made regarding the oxidation compositions or alkalization compositions used as contemplated herein and preferred as contemplated herein also apply mutatis mutandis to the use as contemplated herein.

EXAMPLES 1.1 Blonding Agent Composition

| | Raw material | % by weight |
|---|---|---|
| 1. | Ammonium persulfate + 0.5% $SiO_2$ | 10.0 |
| 2. | Potassium persulfate | 28.2 |
| 3. | Sodium persulfate | 2.0 |
| 4. | Britesil C 265 | 39.0 |
| 5. | Degalan RG S hv | 1.0 |
| 6. | Cekol 50000 | 1.5 |
| 7. | Sodium chloride | 0.5 |
| 8. | Magnesium carbonate solid pharm. 400 g/l | 7.0 |
| 9. | Silicic acid hydrophilic BET | 0.2 |
| 10. | Celquat L-200 | 0.3 |
| 11. | EDETA BX Powder | 1.6 |
| 12. | Sodium percarbonate | 8.0 |
| 13. | Tylose H 100000 YP2 | 1.2 |
| | | 100 |

Table of Raw Materials Used

| | |
|---|---|
| Britesil C 265 | Sodium silicate having $SiO_2/Na_2O$ (molar) of 2.61-2.70 |
| Degalan RG S hv | INCI: Acrylates Copolymer |
| Cekol 50000 | Cellulose Gum |
| Celquat L-200 | Polyquaternium-4 (at least 96% by weight), water (up to 4% by weight) |
| EDETA BX Powder | Tetrasodium EDTA (84.5% by weight), water (15.5% by weight) |
| Tylose H 100000 YP2 | Hydroxyethyl cellulose (94.5% by weight), water (5.5% by weight) |

The powder is mixed with water in a ratio of 1:2 and applied to light brown Fischbach & Miller hair strands for 45 minutes.

The hair was measured colorimetrically after use with a spectrophotometer from Datacolor (SF450) and the color difference (dE76) was determined.

The levels of sodium chloride were changed in the tests of blonding performance. The first composition (batch name

1) did not include NaCl, the second composition (see table above) included 0.5% by weight (+/−0.01% by weight), the further compositions included increasing levels of NaCl, each increasing by 0.5% by weight. In order for the total amount of all ingredients in the composition to still add up to 100% by weight, the weighed amount of magnesium carbonate was reduced by the amount of NaCl weighed in each case.

1.2 Measurement of Blonding

The blonding performance is shown below. The L value indicates the brightness of the color (L=0, black, L=100, white). The higher the L value of the treated strand, the more intensely the strand was blonded.

| Batch name | CIE L | CIE a | CIE b | CIE c | CIE h | CIE dE$_{76}$ |
|---|---|---|---|---|---|---|
| #1—0.0% by weight NaCl | 41.7 | 10.42 | 24.16 | 26.32 | 66.67 | 23.0 |
| #2—0.5% by weight NaCl | 46.49 | 10.50 | 27.06 | 29.03 | 68.80 | 28.5 |
| #3—1.0% by weight NaCl | 42.13 | 10.45 | 24.90 | 27.00 | 67.23 | 23.8 |
| #4—1.5% by weight NaCl | 41.59 | 11.22 | 25.64 | 27.98 | 66.36 | 24.0 |
| #5—2.0% by weight NaCl | 42.77 | 11.27 | 25.48 | 27.87 | 66.14 | 24.8 |
| #6—2.5% by weight NaCl | 42.65 | 10.90 | 25.94 | 28.14 | 67.21 | 24.9 |

The ΔE value (dE76) used for assessing the color intensity results from the L*a*b* colorimetric values as follows:
$$\Delta E = [(L_i - L_0)^2 + (a_i - a_0)^2 + (b_i - b_0)^2]^{1/2}$$
$L_0$, $a_0$ and $b_0$: Color measurement values before blonding
$L_i$, $a_i$ and $b_i$: Color measurement values after blonding The ΔE value indicates the color difference that exists between the untreated and treated hair strands. The larger the dE value, the greater the color difference (that is, the color space) between the undyed and the dyed skin and the stronger the blonding performance.

2. Further Blonding Powder Formulations and their Use (Unless otherwise stated, amounts specified are % by weight)

| | Nr. 1 | Nr. 2 | Nr. 3 | Nr. 4 |
|---|---|---|---|---|
| Potassium persulfate | 32.00 | 32.00 | 32.00 | 32.00 |
| Ammonium persulfate | 9.90 | 9.90 | 9.90 | 9.90 |
| L-arginine | — | 1.00 | — | — |
| Sodium silicate having SiO$_2$/Na$_2$O (molar) of 2.61-2.70 | 35.7 | 32.7 | 31.7 | 29.1 |
| Magnesium hydroxide carbonate | 4.85 | 5.55 | 4.85 | 3.45 |
| Sodium hexametaphosphate | 0.20 | 0.20 | 0.20 | 0.20 |
| Methyl methacrylate / methacrylic acid copolymer | 1.00 | 1.00 | 1.00 | 1.00 |
| Carboxymethylcellulose | 2.00 | 2.00 | 2.00 | 2.00 |
| EDTA Na4 | 0.60 | 1.40 | 0.60 | 0.60 |
| Polyquaternium-10 | — | 0.50 | — | — |
| Hydrophilic silicic acid | 0.40 | 0.40 | 0.40 | 0.40 |
| CI 77007 (Ultramarines) | 0.15 | 0.15 | 0.15 | 0.15 |
| Sodium percarbonate | 8.00 | 8.00 | 12.00 | 16.00 |
| Sodium chloride | 0.3 | 0.3 | 0.3 | 0.3 |
| Paraffinum Liquidum | 4.30 | 4.30 | 4.30 | 4.30 |
| Perfume | 0.60 | 0.60 | 0.60 | 0.60 |
| Total | 100.00 | 100.00 | 100.00 | 100.00 |

The respective blonding powder and the developer emulsion were mixed with each other in a weight ratio of 1:2. In another embodiment of the present disclosure, the respective blonding powders were mixed with water in a weight ratio of 1:2.

2.2 Application 100 g of the freshly prepared mixture of the respective blonding powder and the developer emulsion or 100 g of the freshly prepared mixture of the respective blonding powder and water were applied to dry strands of hair (4 g of application mixture per gram of hair).

After blonding for 45 minutes at 32° C., the strands were rinsed with water for 2 minutes and dried with a hair dryer.

This blonding operation was repeated once, so that the strands were blonded a total of twice in succession.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A blonding agent for changing the natural color of keratinic fibers, comprising
   a) sodium percarbonate,
   b) sodium chloride is present in an amount of from 0.5-0.7% by weight based on the weight of the blonding agent and further
   c) from 0 to about 8% by weight of water based on the weight of the blonding agent;
   wherein the blonding agent is in powder form.

2. The blonding agent according to claim 1, wherein sodium percarbonate is present in an amount of from about 1-50% by weight.

3. The blonding agent according to claim 1, further comprises at least one inorganic salt of peroxosulfuric acid and wherein the at least one inorganic salt of a peroxosulfuric acid is selected from sodium peroxodisulfate, potassium peroxodisulfate, ammonium peroxodisulfate, sodium peroxomonosulfate, potassium peroxomonosulfate, ammonium peroxomonosulfate, or mixtures of these compounds.

4. The blonding agent according to claim 3, wherein the inorganic salt of a peroxosulfuric acid includes a mixture comprising from about 5 to about 40% by weight of ammonium peroxodisulfate based on the total weight of the blonding agent.

5. The blonding agent according to claim 1, further comprising a persulfate, wherein the percarbonate and the persulfate(s) are present separately from one another.

6. The blonding agent according to claim 5, wherein the weight ratio of the amount of percarbonate to the total amount of persulfate(s) is between about 2 to about 1 and about 1 to about 20.

7. The blonding agent according to claim 1, wherein further comprising at least one inorganic alkalizing agent solid at 20° C. and 1013 mbar, wherein the at least one inorganic alkalizing agent is chosen from sodium silicate or sodium metasilicate having a molar SiO$_2$/Na$_2$O ratio of ≥2.

8. The blonding agent according to claim 1, further comprising at least one complexing agent selected from: ethylenediaminetetraacetic acid (EDTA); N-hydroxyethylethylenediaminetriacetic acid; aminotrimethylenephosphonic acid; diethylenetriaminepentaacetic acid; lauroyl ethylenediamine triacetic acid; nitrilotriacetic acid;

iminodisuccinic acid; N-2-hydroxyethyliminodiacetic acid; ethylene glycol-bis-(beta-aminoethyl ether)-N,N-tetraacetic acid; aminotrimethylenephosphonic acid, pentasodium aminotrimethylenephosphonate, and mixtures thereof, in a total amount of from about 0.1-1.4% by weight based on the weight of the blonding agent.

9. The blonding agent according to claim 1, wherein sodium percarbonate is present in an amount of from about 4-10% by weight based on the weight of the blonding agent.

10. The blonding agent according to claim 3, wherein the at least one inorganic salt of a peroxosulfuric acid is included in the blonding agent in an amount of from about 30-50% by weight based on the weight of the blonding agent.

11. The blonding agent according to claim 3, wherein the inorganic salt of a peroxosulfuric acid constitutes a mixture comprising from about 15 to about 30% by weight of potassium peroxodisulfate, from about 10 to about 15% by weight of ammonium peroxodisulfate, and from about 2 to about 20% by weight of sodium peroxodisulfate, in each case based on the total weight of the blonding agent.

12. The blonding agent according to claim 5, wherein the weight ratio of the amount of percarbonate to the total amount of persulfate(s) is between about 1 to 3 and about 1 to 6.

13. The blonding agent according to claim 7, wherein the at least one inorganic alkalizing agent is present in an amount of from about 5 to about 40% by weight based on the weight of the blonding agent.

14. The blonding agent according to claim 8, wherein the at least one complexing agent is present in a total amount of from about 0.5-1.4% by weight based on the weight of the blonding agent.

15. A method for lightening keratinic fibers, wherein a blonding agent according to claim 1 is mixed with water, applied immediately afterwards to the keratin-containing fibers, left on the fibers for from about 5 to about 60 minutes and then the fibers are rinsed with water and optionally washed with a surfactant-containing detergent.

16. The blonding agent according to claim 1, free from hydrogen peroxide.

* * * * *